United States Patent [19]
Pinto

[11] Patent Number: 5,700,783
[45] Date of Patent: Dec. 23, 1997

[54] METHOD OF TREATING URINARY INCONTINENCE

[75] Inventor: Angelo Pinto, Via Roma, 44, Casalvelino (Salerno), Italy

[73] Assignee: Angelo Pinto, Casalvelino, Italy

[21] Appl. No.: 429,213

[22] Filed: Apr. 24, 1995

[30] Foreign Application Priority Data

Apr. 28, 1994 [IT] Italy ................................ SA94A0004

[51] Int. Cl.$^6$ .......................... A61K 38/00; A61K 35/14; A61F 6/06
[52] U.S. Cl. ................... 514/21; 514/2; 514/911; 530/381; 530/382; 530/817; 424/422; 424/430; 424/558
[58] Field of Search ...................... 514/21.2, 911; 530/381, 382, 817; 424/422, 430, 558

[56] References Cited

U.S. PATENT DOCUMENTS 5,516,532  5/1996  Atala et al. ............................ 424/548

OTHER PUBLICATIONS

Taneli et al, *British Journal of Urology*, vol. 74, No. 6, pp. 710–714, 1994.
Claes et al, *The Journal of Urology*, vol. 142, pp. 821–822, Sep. 1987.
Tsurusaki et al, *The Journal of Urology*, vol. 155, p. 1698, May 1966.
Volz et al., *Zentralblatt Für Gynäjikigue*, "Die Endoskopie des präperitonealen Intersitiums—ein neuer zugang für die Kolposuspension", vol. 115, No. 11, pp. 488–491 (1993).
Dellas, *Geburtshilfe Und Frauenheilkunde*, "Kolposuspension mit Fibrinkleber", vol. 53, No. 9, p. 651 (1993).

*Primary Examiner*—Cecilia J. Tsang
*Assistant Examiner*—Abdel A. Mohamed
*Attorney, Agent, or Firm*—Seidel, Gonda, Lavorgna & Monaco, PC

[57] ABSTRACT

A method for treating urinary incontinence consisting of injecting human fibrin glue at or near the bladder neck until the urethral outflow resistance is restored. Human fibrin glue is the reaction product of human fibrinogen and thrombin in the presence of calcium chloride as catalyst.

3 Claims, No Drawings

METHOD OF TREATING URINARY INCONTINENCE

FIELD OF THE INVENTION

The present invention relates to the non-surgical treatment of urinary incontinence due to stress and in particular to a bulking agent to be injected at or near the bladder neck until the urethral outflow resistance is restored.

BACKGROUND OF THE INVENTION

It is known that in stress incontinence urine is involuntarily lost through the urethra after a sudden increase of the inter-abdominal pressure even without a contraction of the detrusor, because of the lack of the complex interactions among the anatomical structures.

In relation to such a disorder, until today, the methods of the art make use of pharmacological remedies such as medicines which strengthen the sphincter tonus, and, above all, of surgical remedies such as colpo-suspension of the bladder neck, use of an artificial sphincter, electrostimulation of the pelvic floor. A non-surgical method has been already developed for treating the stress incontinences which consists injecting a bulking agent near or at the bladder neck. The bulking agent creates an increased tissue bulk and consequent occlusion of the urethral lumen. Polytetrafluoroethylene derivatives which were initially used as a bulking agents were subsequently abandoned because of the high danger of particle migration and the resulting risk of embolism. Another known bulking agent is heterologous collagen which, besides the high cost, has also some limits, i.e. the risk due to the hyperallergenicity of the substance and the resorption tendency of the tissues.

SUMMARY OF THE INVENTION

It is therefore an object of the present invention to supply a new bulking agent for the non-surgical treatment of stress incontinence, which is less expensive than heterologous collagen and without any risk of allergies. This object is achieved by using human fibrin glue as a bulking agent.

Accordingly, a method of treating urinary incontinence is provided. An effective amount of human fibrin glue is injected into the submucosal tissues of the urethra, bladder neck, or both.

DETAILED DESCRIPTION OF THE INVENTION

Human fibrin glue is the reaction product of human fibrinogen and thrombin in presence of calcium chloride as catalyst. Human fibrin glue is well known as a complement for surgical sutures and is used for its heamostatic activity, its adhesive capacity as well as for its biostimulating and tissue regenerating capacity due to the presence of fibronectine.

The human fibrin glue can be injected either periurethrally or interurethrally in order to increase the urethral pressure and compensate sphincter weakness. The interurethral injections are preferred because they are practically painless. The injection of human fibrin glue into the submucosal tissues of the urethra or of the bladder neck creates the desired increased tissue bulk, and the consequent restoration of the urethral resistance to the involuntary loss of urine.

Experimentation was carried out on an outpatient basis, in all cases interurethrally, without local anaesthesia and under direct cytoscopic vision. Human fibrin glue was injected in 20 females into the urethral muscolar layer at the 6 o'clock position, from just below the bladder neck to 1-2 cm distally in the urethra. In 3 male patients, the human fibrin glue was injected immediately over the membranous urethra at 3, 6, 9 and 12 o'clock positions. The human fibrin glue used in this experimentation is marketed by the Austrian company Immuno GmbH under the trademark "TISSUCOL".

In all cases the treatment was interrupted when a good occlusion of the urethral lumen was obtained. In many cases a good occlusion of the urethral lumen was obtained after the first injection. In some cases the injection was repeated after having checked the patient's urethral resistance after a fit of coughing. The average amount of human fibrin glue injected in the patient experimentation was 5.9 ml, and the range was maintained from 5 to 15 ml. The recommended range is from 5 to 10 ml. The dosage does not depend on the weight of the patient, but of the lumen of the bladder neck under stress. A wider lumen requires a higher dosage.

The post operative evaluation was comprehensive of urethral pressory profile study. Maximum follow up was 16 months, minimum 6 months, with an average of 8.3 months. In the female group of patients treated according to the present invention good results were observed in 15 patients, partially good results in 3 patients and poor results in 2 patients. In the male group of patients with urethral failures after radical prostatectomy (2 cases) or cystectomy (1 case) good results were observed in the first group.

The practical experimentation of the use of human fibrin glue in the treatment of stress incontinence has confirmed one of the enormous advantages connected thereto, i.e. the low cost of the human fibrin glue with respect to the use of collagen as a bulking agent. Human fibrin glue is 5 to 10 times cheaper than bovine collagen.

Another advantage connected with the use of human fibrin glue in the treatment of stress incontinence is that human fibrin glue, being a derivative of human blood, does not have any allergic effect, thus reducing the risks connected with its use and the cases of inapplicability. Moreover, the biostimulating activity of the human fibrin glue stimulates fibroplast formation and, as it appears believable from the experiments described above, regenerates the tissue which should stably restore the urethral resistance to the involuntary loss of urine.

What I claim is:

1. A method of treating urinary incontinence comprising injecting a human fibrin glue into the submucosal tissues of the urethra, bladder neck, or both, of a patient in need of such treatment.

2. Method according to claim 1 wherein said human fibrin glue is injected interurethrally.

3. A method according to claim 1 wherein said human fibrin glue is injected periurethrally.

* * * * *